Jan. 14, 1941. H. C. SWIM Plant Pat. 439

HYBRID TEA ROSE PLANT

Filed July 26, 1940

INVENTOR
Herbert C. Swim
By Orville M. Kile
Plant Patent Agt

Patented Jan. 14, 1941

Plant Pat. 439

UNITED STATES PATENT OFFICE

439

HYBRID TEA ROSE PLANT

Herbert C. Swim, Ontario, Calif., assignor to Armstrong Nurseries, Inc., Ontario, Calif.

Application July 26, 1940, Serial No. 347,751

1 Claim. (Cl. 47—61)

My new variety originated as a bud sport of the rose Night, discovered by me in the gardens of Armstrong Nurseries, Inc.

The most clearly distinguishing feature of this new rose plant is its vigorous growing habit, its strong canes attaining a length of 12 to 14 feet or more as distinguished from the usual height of 3 or 4 feet attained by the bush form of the rose Night. Because of the much larger plant produced, the new variety carries many more flowers in the spring than can be found at any one time on the bush variety Night.

The flowers of the new variety are usually larger in size and petalage than the flowers found on the bush Night, there being from 7 to 12 petals and 3 or 4 petaloids more in the flowers of the new variety, grown under the same conditions. No novelty of color of the bud or blossom is claimed.

The new variety has been asexually reproduced for several years and these characteristics have proved to be permanently fixed.

Figure 2:
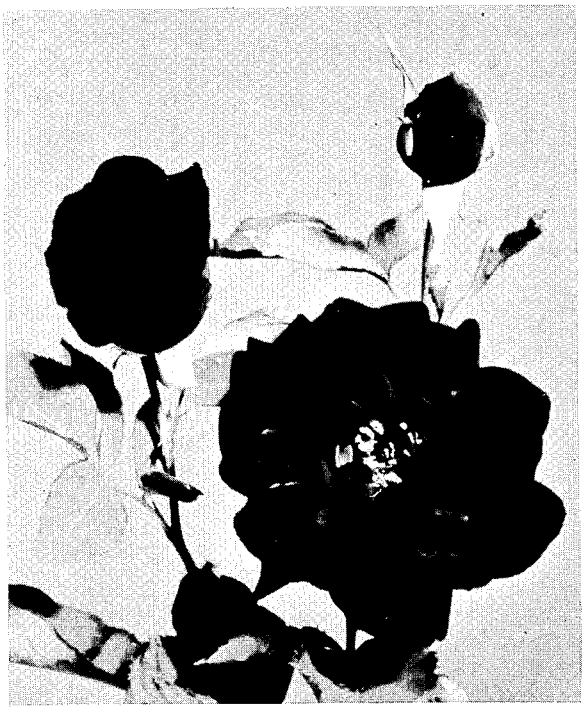
Figure 1:
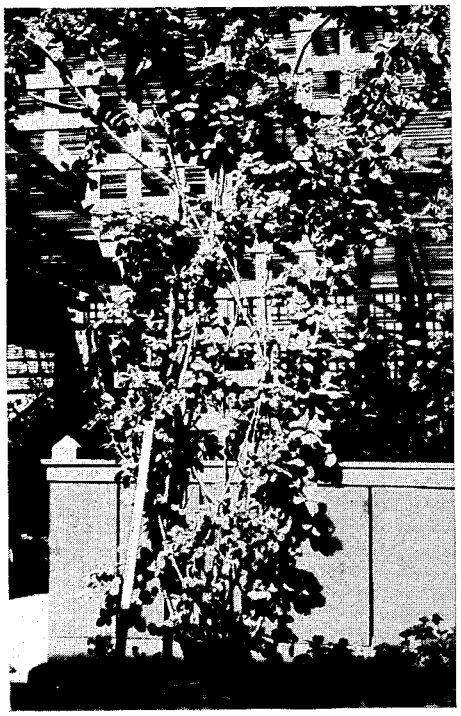

The illustration accompanying this application shows in Fig. 1 a two years' growth of a specimen of this new variety of rose plant together with a yardstick set up beside it to indicate its vigorous, climbing growth. Fig. 2 is a photograph of three specimen flowers of this variety in various stages of opening.

Following is a detailed description of the plant and flower of this new variety of rose plant. Colors are indicated by reference to Ridgway's Color Standards and Nomenclature except where it is obvious that the ordinary dictionary meaning is intended.

*The plant*

Growth habit: Vigorous climber, sending out stout canes which are frequently more than ten feet in length.

Blooming habit: Largest burst of bloom is in the spring but there are occasional flowers throughout the rest of the season. Flowers usually borne singly.

Disease resistance: The resistance of this variety to most diseases common to roses is similar to that of bush Night, although the new variety is somewhat more resistant to mildew.

Foliage: Profuse; large; leaves pinnate, 5 to 6 inches long; five leaflets.

*Texture.*—Leathery and of medium thickness.

*Color.*—Dark green above; lighter green verging on gray-green below. Young foliage reddish purple.

*Shape.*—Leaflets ovate with mucronate tip; sometimes nearly round.

*Margin.*—Somewhat undulating. Pronounced serration near tip of leaflet, becoming less pronounced progressively toward the base.

*Petiole.*—Usually about one inch long.

*Rachis.*—Upper surface lined with thinly spaced, short, glandular hairs. Under surface usually glabrous, sometimes having two or three very small, hooked thorns which are pink when young and age to near white.

*Thorns.*—Occasional prickles and many short, strong, hooked thorns on canes; Carmine (Plate I) when young, aging to light brown.

*Sepals.*—Usually slightly foliaceous, tendency increasing in vigorous state of growth; wedge-shaped; ¾ to 1 inch long; reflexed early in bud stage.

*The flower*

Bud:

*Form.*—Ovoid.

*Size.*—Medium; approximately 1¼ to 1½ inches long and ¾ inch in diameter at thickest point.

*Color.*—Same as bush Night. Approximately Pomegranate Purple (Plate XII) with Violet Carmine (Plate XII) on tips.

*Peduncle.*—Short; adequate; covered with numerous short, gland-tipped hairs.

Blossom:

*Form.*—Same as bush Night; cup-shaped center with petals inclined to be flat, rolling under slightly at margins as flower ages. All petals rather wide.

*Size.*—Averages 3½ to 4 inches in diameter.

*Petalage.*—Twenty-five to thirty petals and three or four petaloids. This is a greater number of petals than found in the flowers of the bush Night.

*Color.*—Rose Red (Plate XII) to Pomegranate Purple, with Violet Carmine on tips of petals. Almost the same as bush Night.

*Texture.*—Fine and of uniform, medium thickness.

*Fragrance.*—Rich cinnamon fragrance.

Reproductive Organs:

*Pistils.*—Bunched; short.

*Stamens.*—Surround pistils. *Filaments*—pink. *Anthers*—straw color.

*Receptacle.*—Glabrous above, with gland-tipped hairs at base.

Having disclosed my discovery, I claim:

A new and distinct variety of hybrid tea rose plant substantially as shown and described, characterized particularly by its climbing habit; its habit of producing a great quantity of blossoms in the spring and blooming intermittently throughout the season; its greater resistance to mildew than shown by its parent; and its flowers similar to those of its parent, the bush Night, but of greater petalage and larger size.

HERBERT C. SWIM.